United States Patent [19]

Zhou et al.

[11] Patent Number: 6,107,508
[45] Date of Patent: Aug. 22, 2000

[54] CONVERGENT SYNTHESIS OF α-ARYL-β-KETONITRILES

[75] Inventors: Jiacheng Zhou, Hockesin; Lynette May Oh, New Castle, both of Del.; Philip Ma, Chadds Ford, Pa.

[73] Assignee: Dupont Pharmaceuticals Company, Wilmington, Del.

[21] Appl. No.: 09/282,508

[22] Filed: Mar. 31, 1999

Related U.S. Application Data

[60] Provisional application No. 60/080,680, Apr. 3, 1998.
[51] Int. Cl.$^7$ ............... C07C 253/00; C07D 279/10; C07D 265/30; C07D 211/60; C07D 207/04
[52] U.S. Cl. ............ 558/309; 558/355; 558/401; 544/58.1; 544/175; 544/395; 546/230; 548/577
[58] Field of Search ............ 558/355, 401, 558/309; 544/58.1, 175, 395; 546/230; 548/577

[56] References Cited

U.S. PATENT DOCUMENTS 4,797,492  1/1989  Sumimoto et al. ............ 548/245

OTHER PUBLICATIONS

Mitchell, Reginald; Lai, Yee–Hing; and Williams, Richard, N–Bromosuccinimide–Dimethylformamide: A Mild Selective Nuclear Monobromination Reagent for Reactive Aromatic Compounds, *J. Org. Chem.*, 44, 4733–4735, Jul. 2, 1979.

Olah, George; Wang, Qi; Sandford, Graham and Prakash, G. K. Surya, Iodinationof Deactivated Aromatics with N–Iodosuccinimide in Trifluoromethanesulfonic Acid via in Situe Generated Superelectrophilic Iodine Trifluoromethanesulfonate, *J. Org. Chem.*, 58, 3894–3195, Jan. 5, 1993.

Rouiller, Charles A., Heterocyclic Compounds—More than One Hetero Atom, CA, 3465–3468, 1962.

Dominguez, Ester; Ibeas, Estibaliz; Martinez de Marigorta, Eduardo; Kepa Palacios, Jon; and SanMartin, Raul, A Convenient One–Pot Preparative Method for 4,5–Diarylisoxazoles Involving Amine Exchange Reactions, *J. Org. Chem*, 61, 5435–5439, 1966.

Sakakibara, Tsutomu; Kume, Takashi; and Hase, Tsunao, Halogenation of Isoxazoles, *Chem. Express*, 4, 85–88, 1989.

Labadie, Sharada, 3–Aryl–2,4,–Pentanediones From 3,5–Dimethyl–4–Iodoisoxazoles: An Application of a Palladium–Catalyzed Cross–Coupling Reaction, *Synthetic Communications*, 24(5), 709–719, 1994.

*Primary Examiner*—Richard L. Raymond
*Assistant Examiner*—Tamthom N. Truong
*Attorney, Agent, or Firm*—Peter L. Dolan

[57] ABSTRACT

The present invention relates to processes for the production of α-aryl-β-ketonitriles, which serve as synthetic intermediates in the preparation of a series of biologically important molecules such as corticotropin releasing factor (CRF) receptor antagonists.

4 Claims, No Drawings

CONVERGENT SYNTHESIS OF α-ARYL-β-KETONITRILES

This application claims the benefit of U.S. Provisional Application No. 60/080,680, filed Apr. 3, 1998.

FIELD OF THE INVENTION

This invention relates to a general and convergent synthesis of α-aryl-β-ketonitriles. Base-promoted isomerization of 3-unsubstituted-4-arylisoxazoles, followed by acidification of the resulting enolates provides the title α-aryl-β-ketonitriles. The corresponding 3-unsubstituted-4-arylisoxazoles were prepared from cross coupling reaction between 4-iodo-5-substituted isoxazole or 4-bromo-5-substituted isoxazole and arylboronic acids under the influence of a suitable catalyst. The α-aryl-β-ketonitriles of the present invention serve as synthetic intermediates in the preparation of a series of biologically important molecules such as corticotropin releasing factor (CRF) receptor antagonists.

BACKGROUND

α-Aryl-β-ketonitriles are important building blocks in the construction of complicated molecular system including natural products and biologically important molecules. They are generally prepared from condensation of α-aryl acetonitriles with the corresponding alkyl carboxylates in the presence of a base, such as sodium ethoxide (Scheme 1) (*J. Am. Chem. Soc.* 1951, 73, 3763; *J. Med. Chem.* 1991, 34, 1721). However, α-arylacetonitriles, which are usually prepared from cyanation of the corresponding benzyl halides, sometimes are not readily accessible due to the substitution pattern on the corresponding aromatic ring.

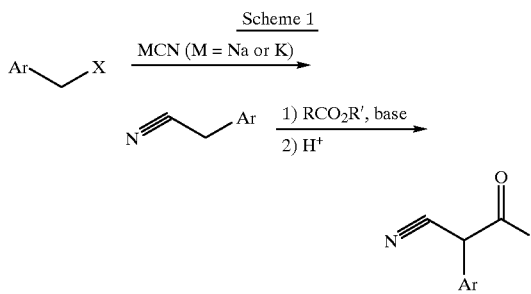

3-Unsubstituted isoxazoles may be cleaved by bases (*Advances in Heterocyclic Chemistry*, 1979, 25, 147; *Tandem Organic Reactions*, 1992, 288; *Tetrahedron Lett.* 1986, 27, 2027; *J. Org. Chem.* 1996, 61, 5435). Claisen showed that treatment of 5-phenylisoxazole with sodium ethoxide in absolute ethanol or with aqueous sodium hydroxide at room temperature yields, after acidification, ω-cyanoacetophenone (*Ber.* 1891, 24, 130). Isoxazole itself is cleaved to the sodium salt of cyanoacetaldehyde (*Ber.* 1903, 36, 3664). The isomerization of 3-unsubstituted isoxazoles to α-cyano carbonyl compounds under the influence of bases takes place readily at room temperature (Scheme 2).

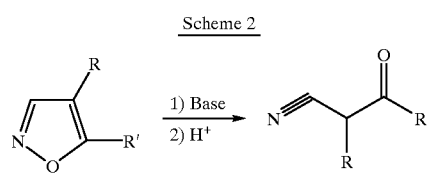

Kinetic studies on the isomerization of 3-unsubstituted isoxazoles have established that the reaction is second order (first order in base and in substrate) and that the mechanism of the reaction belongs to a concerted one-stage E2 type rather than to a two-step E1cB type (Scheme 3) (*Gazz. Chim. Ital.* 1960, 90, 356; *Chim. Ind.* (*Milan*), 1966, 48, 491; *Gazz. Chim. Ital.* 1967, 97, 185). The effective isolation of the α-cyanoketone, however, depends on the stability of the latter compound, which is often unstable and readily dimerizes and/or polymerizes (*Helv. Chim. Acta*, 1963, 46, 543; Ger. Offen. 2,623,170; *Chem. Abstr.* 1978, 88, 62159).

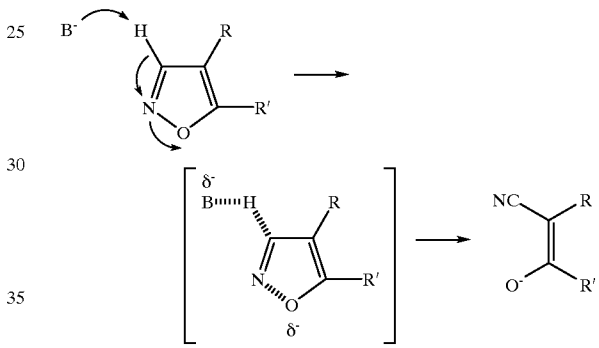

The α-aryl-β-ketonitriles of the present invention serve as synthetic intermediates in the preparation of a series of biologically important molecules such as corticotropin releasing factor (CRF) receptor antagonists. The present invention describes a process for preparing 3-unsubstituted 4-aryl-isoxazoles and their use in preparing α-aryl-β-ketonitriles. Although methods are available for the preparation of some substituted isoxazoles, selective, high-yielding methods which produce pure crude intermediates for the preparation of 3-unsubstituted 4-arylisoxazoles are unknown in the art.

The present invention describes a convergent preparation of substituted α-aryl-β-ketonitriles (I).

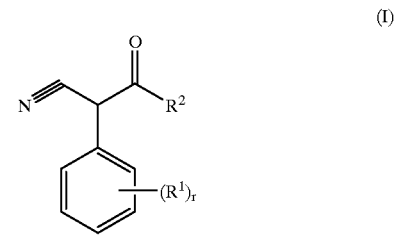

The process includes reacting a substituted isoxazole with a halogenating agent to give a haloisoxazole (Scheme 4).

Scheme 4

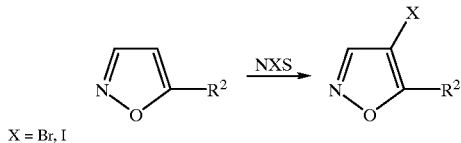

X = Br, I

The literature teaches the synthesis of 4-iodo-5-methylisoxazole by iodination of 5-methylisoxazole with $I_2$ in the presence of a oxidizing agent such as concentrated nitric acid but gives poor conversion under the reported optimized conditions. The present invention discloses an efficient synthesis of 4-iodo-5-methylisoxazole by treating commercially available 5-methylisoxazole with NIS in strong organic acidic medium, such as trifluroacetic acid, which results in an unexpected yield and purity which is critical for commercial drug preparation.

The present invention also discloses an efficient and regioselective aromatic bromination method for the effective production of the brominated aromatic compound. A phenyl group containing an electron donating functionality in the aromatic ring, is reacted with N-bromosuccinimide followed by reacting the lithium salt of the product with a alkylborate in situ to produce a phenyl boronic after acidic hydrolysis (Scheme 5). This intermediate is coupled directly with the haloisoxale to give the isomerization precursor (Scheme 6).

Scheme 5

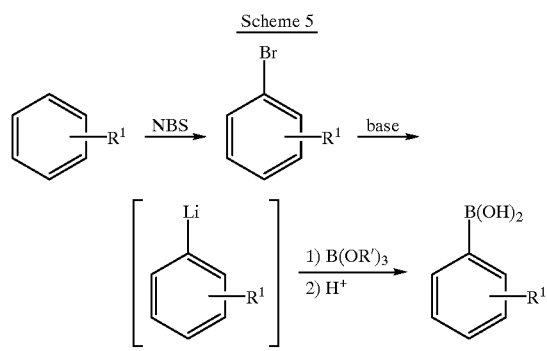

Scheme 6

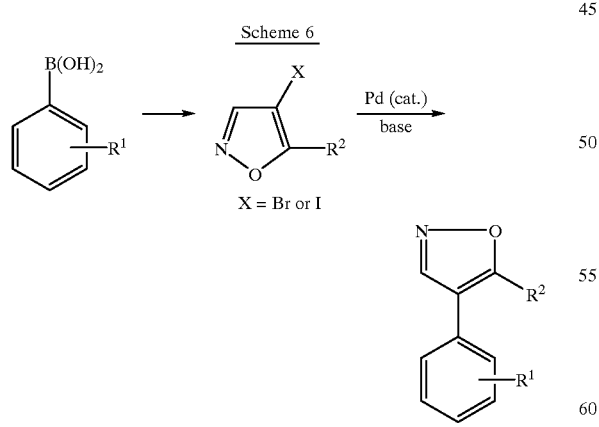

X = Br or I

Finally, a very efficient protocol for the isomerization of 4-aryl substituted isoxazoles to the corresponding α-aryl-β-ketonitriles under the influence of a base, such as sodium methoxide is described. (Scheme 7). Due to the efficiency of the preceeding reaction, a crude cross coupling product can be used to conduct this base-promoted isomerization reaction, providing the corresponding α-aryl-β-ketonitriles directly, with exceptional purity which is beneficial for large-scale preparation of the drug substance.

Scheme 7

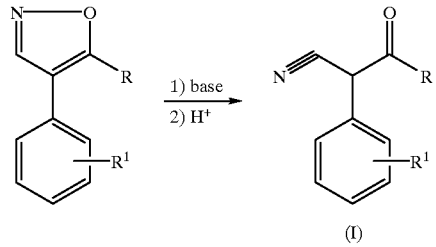

(I)

Commonly-assigned U.S. provisional application 08/899, 242, filed Jul. 23, 1997, disclosed 2,4,7,8-tetra-substituted pyrazolo[1,5-a]-1,3,5-triazines derivatives and their use in treating CRF-related abnormalities. By improving the core structure synthesis, a convergent, and therefore more efficient synthesis has been developed. This general synthetic method has been successfully used in the large-scale synthesis of this important class of corticotropin releasing factor (CRF) receptor antagnists.

SUMMARY OF THE INVENTION

The present invention relates generally to processes for the conversion of α-aryl-β-ketonitriles to pyrazolo [1,5-a]-1,3,5-triazine derivatives for the purpose of producing compounds, and intermediates therefore, which are useful antagonists of the corticotropin releasing factor (CRF) receptor. These compounds may be used for the treatment of (CRF) related abnormalities such as depression and anxiety. There is provided by this invention a process for the preparation of compounds of formula (I), (III), (IV), (V) and (VI):

(I)

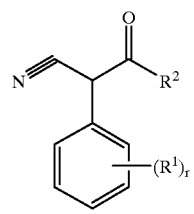

(II)

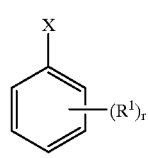

(III)

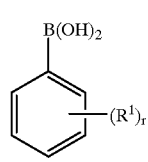

-continued

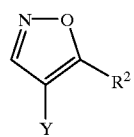
(V)

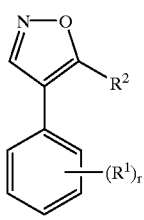
(VI)

wherein:
r is an integer from 0 to 4;
$R^1$ is independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NR^{1c}R^{1d}$, —$OR^{1e}$, and —$SR^{1e}$;
$R^{1c}$ and $R^{1d}$ are independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl;
alternatively, $R^{1c}$ and $R^{1d}$ are taken together to form a heterocyclic ring selected from the group consisting of: piperidine, pyrrolidine, piperazine, N-methylpiperazine, morpholine and thiomorpholine, each heterocyclic ring optionally substituted with 1–3 $C_1$–$C_4$ alkyl groups;
$R^{1e}$ is independently selected at each occurrence from the group consisting of:
H, $C_1$–$C_{10}$ alkyl, $C_3$–$C_6$ cycloalkyl, and $C_4$–$C_6$ cycloalkylalkyl;
$R^2$ is selected from the group consisting of:
H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;
$R^{2a}$ is independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, —$OR^{2e}$, and —$SR^{2e}$; and
$R^{2e}$ is independently selected at each occurrence from the group consisting of:
H, $C_1$–$C_{10}$ alkyl, $C_3$–$C_6$ cycloalkyl, and $C_4$–$C_6$ cycloalkylalkyl;
said process comprising the steps of:
(1) contacting a compound of formula (II):

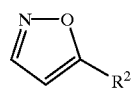
(II)

with a suitable halogenating agent to form a compound of formula (III);
(2) contacting the compound of formula (III) with alkylborate in the presence of a strong base to give a compound of formula (IV) after acidic hydrolysis;
(3) contacting the compound of formula (IV) with a compound of formula (V) in the presence of a catalyst and a suitable weak base to give a compound of formula (VI); and
(4) contacting the compound of formula (VI) with an isomerization base to give a compound of formula (I), or a pharmaceutically acceptable salt form thereof.

DETAILED DESCRIPTION OF THE INVENTION

In a first embodiment, the present invention provides a process for the preparation of compounds of formula (I):

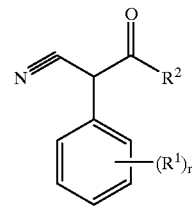
(I)

or a pharmaceutically acceptable salt form thereof;
wherein:
r is an integer from 0 to 4;
$R^1$ is independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NR^{1c}R^{1d}$, —$OR^{1e}$ and —$SR^{1e}$;
$R^{1c}$ and $R^{1d}$ are independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl;
alternatively, $R^{1c}$ and $R^{1d}$ are taken together to form a heterocyclic ring selected from the group consisting of: piperidine, pyrrolidine, piperazine, N-methylpiperazine, morpholine and thiomorpholine, each heterocyclic ring optionally substituted with 1–3 $C_1$–$C_4$ alkyl groups;
$R^{1e}$ is independently selected at each occurrence from the group consisting of:
H, $C_1$–$C_{10}$ alkyl, $C_3$–$C_6$ cycloalkyl, and $C_4$–$C_6$ cycloalkylalkyl;
$R^2$ is selected from the group consisting of:
H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;
$R^{2a}$ is independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, $OR^{2e}$, and —$SR^{2e}$; and
$R^{2e}$ is independently selected at each occurrence from the group consisting of:
H, $C_1$–$C_{10}$ alkyl, $C_3$–$C_6$ cycloalkyl, and $C_4$–$C_6$ cycloalkylalkyl;
the process comprising the steps of:

(1) contacting a compound of formula (II):

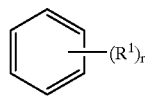

(II)

with a halogenating agent to form a compound of formula (III):

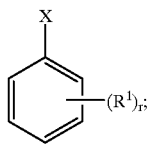

(III)

wherein X is a halogen derived from the halogenating agent;

(2) contacting the compound of formula (III) with a strong base followed by addition of an alkylborate to form a compound of formula (IV):

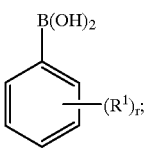

(IV)

(3) contacting the compound of formula (IV) with a compound of formula (V):

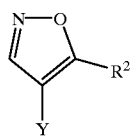

(V)

wherein Y is a second halogen;
in the presence of a catalyst and a weak base to form a compound of formula (VI):

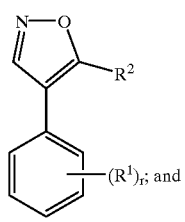

(VI)

(4) contacting the compound of formula (VI) with an isomerization base to form a compound of formula (I), or a pharmaceutically acceptable salt form thereof.

In a preferred embodiment, r is an integer from 0–3; X is bromine; Y is iodine; $R^1$ is independently selected at each occurrence from the group consisting of hydrogen, methyl and methoxy; and $R^2$ is methyl.

In another preferred embodiment, in step 1, the halogenating agent is N-bromosuccinimide and X is bromine;

in step 2, the alkylborate is selected from the group consisting of:
trimethylborate, triethylborate, tripropylborate, triisopropylborate, tributylborate, triisobutylborate, tri-sec-butylborate, and tri-t-butylborate;

the strong base is selected from the group consisting of:
isobutyllithium, n-hexyllithium, n-octyllithium, n-butyllithium, s-butyllithium, t-butyllithium, phenyllithium and triphenylmethyllithium;

in step 3, the weak base is a phosphate buffer having a pH of about 7 to about 10 or sodium bicarbonate;

Y is iodine;

the catalyst is tetrakis(triphenylphosphine) palladium(0) or [1,1'-Bis(diphenylphosphino)ferrocene] palladium (II) chloride; and in step 4, the isomerization base is selected from the group consisting of:
lithium methoxide, sodium methoxide, potassium methoxide, lithium ethoxide, sodium ethoxide, potassium ethoxide, lithium tert-butoxide, sodium tert-butoxide, and potassium tert-butoxide.

In a more preferred embodiment, the halogenating agent is N-bromosuccinimide, the alkylborate is triisopropylborate, the strong base is n-butyllithium, the catalyst is [1,1'-Bis(diphenylphosphino) ferrocene] palladium (II) chloride, the weak base is sodium bicarbonate, the isomerization base is sodium methoxide, and the compound of formula (I) is:

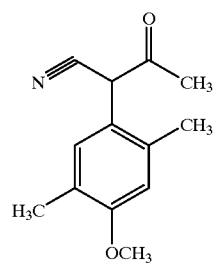

(I)

or a pharmaceutically acceptable salt form thereof.

In another preferred embodiment, the compound of formula (V) is prepared by contacting a compound of formula (VII):

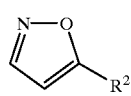

(VII)

with a second halogenating agent to give a compound of formula (V)

In a second embodiment, the present invention describes a process for the preparation of a compound of formula (V):

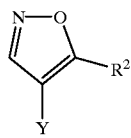

wherein:
  Y is a halogen
  $R^2$ is selected from the group consisting of:
    H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;
  $R^{2a}$ is independently selected from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, —$OR^{2e}$ and —$SR^{2e}$;
  $R^{2e}$ is selected from the group consisting of:
    H, $C_1$–$C_{10}$ alkyl, $C_3$–$C_6$ cycloalkyl, and $C_4$–$C_6$ cycloalkylalkyl;

the process comprising contacting a compound of formula (VII):

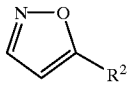

with a halogenating agent in an organic acid to form a compound of formula (V).

In a preferred embodiment, $R^2$ is methyl, the halogenating agent is N-iodosuccinimide, and the organic acid is triflouroacetic acid.

In a third embodiment, the present invention provides a process for the preparation of a compound of formula (I):

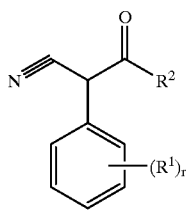

or a pharmaceutically acceptable salt form thereof; wherein:
  r is an integer from 0 to 4;
  $R^1$ is independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NR^{1c}R^{1d}$, —$OR^{1e}$, and —$SR^{1e}$;
  $R^{1c}$ and $R^{1d}$ are independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl;
  alternatively, $R^{1c}$ and $R^{1d}$ are taken together to form a heterocyclic ring selected from the group consisting of: piperidine, pyrrolidine, piperazine, N-methylpiperazine, morpholine and thiomorpholine, each heterocyclic ring optionally substituted with 1–3 $C_1$–$C_4$ alkyl groups;
  $R^{1e}$ is selected from the group consisting of:
    H, $C_1$–$C_{10}$ alkyl, $C_3$–$C_6$ cycloalkyl, and $C_4$–$C_6$ cycloalkylalkyl;
  $R^2$ is selected from the group consisting of:
    H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;
  $R^{2a}$ is independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, —$OR^{2e}$, and —$SR^{2e}$; and
  $R^{2e}$ is independently selected at each occurrence from the group consisting of:
    H, $C_1$–$C_{10}$ alkyl, $C_3$–$C_6$ cycloalkyl, and $C_4$–$C_6$ cycloalkylalkyl;

the process comprising the steps of:
  (1) contacting a compound of formula (IV):

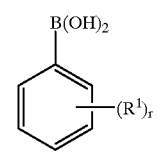

with a compound of formula (V):

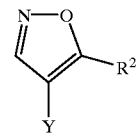

wherein Y is a halogen;
  in the presence of a catalyst and a weak base to give a compound of formula (VI):

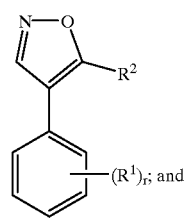

(2) contacting the compound of formula (VI) with an isomerization base to give a compound of formula (I), or a pharmaceutically acceptable salt form thereof.

In a preferred embodiment, r is an integer from 0–3, Y is iodine, $R^1$ is independently selected at each occurrence from the group consisting of hydrogen, methyl and methoxy, and $R^2$ is methyl.

In another preferred embodiment, in step 1, the weak base is sodium bicarbonate or a phosphate buffer with pH of about 7 to about 10;
  the catalyst is tetrakis(triphenylphosphine)palladium(0) or [1,1'-Bis(diphenylphosphino)ferrocene] palladium (II) chloride; and in step 2, the isomerization base is selected from the group consisting of:
lithium methoxide, sodium methoxide, potassium methoxide, lithium ethoxide, sodium ethoxide, potassium ethoxide, lithium tert-butoxide, sodium tert-butoxide, and potassium tert-butoxide.

In a more preferred embodiment, the weak base is sodium bicarbonate, the catalyst is [1,1'-Bis(diphenyl-phosphino) ferrocene] palladium (II) chloride, and the isomerization base is sodium methoxide.

In a fourth embodiment, the present invention provides a process for the preparation of a compound of formula (VI):

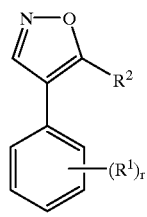
(VI)

or a pharmaceutically acceptable salt form thereof;
wherein:

r is an integer from 0 to 4;

$R^1$ is independently selected at each occurrence from the group consisting of:
H, $C_1$–$C_{10}$ alkyl, $C_2$–$C_{10}$ alkenyl, $C_2$–Cl1 alkynyl, $C_3$–$C_6$ cycloalkyl, $C_4$–$C_{12}$ cycloalkylalkyl, —$NR^{1c}R^{1d}$, —$OR^{1e}$ and —$SR^{1e}$;

$R^{1c}$ and $R^{1d}$ are independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl;

alternatively, $R^{1c}$ and $R^{1d}$ are taken together to form a heterocyclic ring selected from the group consisting of:
piperidine, pyrrolidine, piperazine, N-methylpiperazine, morpholine and thiomorpholine, each heterocyclic ring optionally substituted with 1–3 $C_1$–$C_4$ alkyl groups;

$R^{1e}$ is selected from the group consisting of:
H, $C_1$–$C_{10}$ alkyl, $C_3$–$C_6$ cycloalkyl, and $C_4$–$C_6$ cycloalkylalkyl;

$R^2$ is selected from the group consisting of:
H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;

$R^{2a}$ is independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, —$OR^{2e}$, and —$SR^{2e}$; and $R^{2e}$ is independently selected at each occurrence from the group consisting of:
H, $C_1$–$C_{10}$ alkyl, $C_3$–$C_6$ cycloalkyl, and $C_4$–$C_6$ cycloalkylalkyl;

the process comprising contacting a compound of formula (IV):

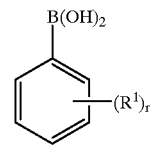
(IV)

with a compound of formula (V):

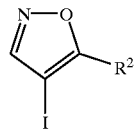
(V)

in the presence of [1,'-Bis(diphenylphosphino)ferrocene] palladium (II) chloride, sodium bicarbonate and a suitable solvent to give a compound of formula (VI).

In a preferred embodiment, $R^2$ is methyl, the suitable solvent is tert-butyl methyl ether, and the compound of formula (IV) is:

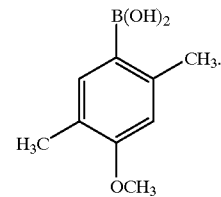
(IV)

In a fifth embodiment, the present invention describes a compound of formula (VI):

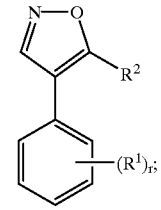
(VI)

wherein:

r is an integer from 0 to 4;

$R^1$ is independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NR^{1c}R^{1d}$, —$OR^{1e}$, and —$SR^{1e}$;

$R^{1c}$ and Rid are independently selected at each occurrence from the group consisting of:
H, $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl;

alternatively, $R^{1c}$ and $R^{1d}$ are taken together to form a heterocyclic ring selected from the group consisting of:
piperidine, pyrrolidine, piperazine, N-methylpiperazine, morpholine and thiomorpholine, each heterocyclic ring optionally substituted with 1–3 $C_1$–$C_4$ alkyl groups;

$R^{1e}$ is independently selected at each occurrence from the group consisting of:
  H, $C_1$–$C_{10}$ alkyl, $C_3$–$C_6$ cycloalkyl, and $C_4$–$C_6$ cycloalkylalkyl;

$R^2$ is selected from the group consisting of:
  H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;

$R^{2a}$ is independently selected at each occurrence from the group consisting of:
  H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, —$OR^{2e}$, and —$SR^{2e}$; and $R^{2e}$ is independently selected at each occurrence from the group consisting of:
  H, $C_1$–$C_{10}$ alkyl, $C_3$–$C_6$ cycloalkyl, and $C_4$–$C_6$ cycloalkylalkyl.

In a sixth embodiment, the present invention describes a compound of formula (I):

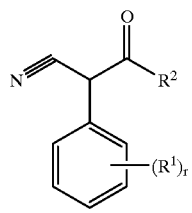

(I)

wherein:
  r is an integer from 0 to 4;
  $R^1$ is independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NR^{1c}R^{1d}$, —$OR^{1e}$ and $SR^{1e}$;
  $R^{1c}$ and $R^{1d}$ are independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl;
  alternatively, $R^{1c}$ and $R^{1d}$ are taken together to form a heterocyclic ring selected from the group consisting of: piperidine, pyrrolidine, piperazine, N-methylpiperazine, morpholine and thiomorpholine, each heterocyclic ring optionally substituted with 1–3 $C_1$–$C_4$ alkyl groups;
  $R^{1e}$ is independently selected at each occurrence from the group consisting of:
    H, $C_1$–$C_{10}$ alkyl, $C_3$–$C_6$ cycloalkyl, and $C_4$–$C_6$ cycloalkylalkyl;
  $R^2$ is selected from the group consisting of:
    H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;
  $R^{2a}$ is independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, —$OR^{2e}$, and —$SR^{2e}$; and
  $R^{2e}$ is independently selected at each occurrence from the group consisting of:
    H, $C_1$–$C_{10}$ alkyl, $C_3$–$C_6$ cycloalkyl, and $C_4$–$C_6$ cycloalkylalkyl.

DEFINITIONS

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

The following terms and abbreviations are used herein and defined as follows. The abbreviation: "THF" as used herein means tetrahydrofuran, "DMF" as used herein means N,N-dimethylformamide, "TBME" as used herein means tert-butyl methyl ether, "HPLC" as used herein means high performance liquid chromatograpy.

Suitable halogenated solvents include: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include: benzene, cyclohexane, pentane, hexane, toluene, cycloheptane, methylcyclohexane, heptane, ethylbenzene, m-, o-, or p-xylene, octane, indane, nonane, or naphthalene.

As used herein, "water immiscible organic solvents" are any of those solvents known in the art of organic synthesis to be suitable for aqueous work-up which are immiscible with water and capable of dissolving organic constituents. Examples include, but are not limited to chlorinated, hydrocarbon, ether, and hydrocarbon solvents.

As used herein, "aqueous acids" include, but are not limited to hydrochloric acid, hydrobromic acid, sulfuric acid, nitric acid, phosphoric acid, lithium, potassium, and sodium bisulfate, and ammonium chloride.

As used herein, "organic acid" includes, but is not limited to formic acid, acetic acid, propionic acid, butanoic acid, methanesulfonic acid, p-toluene sulfonic acid, trifluorosulfonic acid, benzenesulfonic acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

As used herein, "weak base" includes, but is not limited to lithium, sodium, potassium bicarbonates, and buffers capable of buffering the solution to pH 6–10, by way of example, but without limitation, phosphate buffers, and borate buffers.

As used herein, "isomerization base" means any base capable of opening of a 3-unsubstituted isoxazoline ring to afford a beta-ketonitrile. Examples of such bases include, but are not limited to: lithium, sodium and potassium salts of methyl, ethyl and t-butyl oxides and lithium, sodium, and potassium hydrides.

As used herein, the term "strong base" refers to any agent which effects a halogen metal exchange in a halophenyl group. Examples of such strong bases include, but are not limited to, alkyllithiums, metal amides, metal hydrides, metal dialkylamides and arylamines, wherein; alkoxides include lithium, sodium and potassium salts of methyl, ethyl and t-butyl oxides; alkyllithiums include, isobutyllithium, n-hexyllithium, n-octyllithium, n-butyllithium, s-butyllithium, t-butyllithium, phenyllithium and triphenylmethyllithium; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

As used herein, "halogenating agents" are those known in the art of organic synthesis capable of donating a halogen to an aromatic system such as isoxazole or phenyl. Such agents include but are not limited to chlorine, bromine, iodine, N-iodosuccinimide, N-chlorosuccinimide and N-bromosuccinimide.

As used herein, "catalyst" includes those which are known in the art of organic synthesis to facilitate a coupling reaction between a haloaryl group and a phenylboronic acid. Examples of such catalysts include but are not limited to, palladium catalysts such as tetrakis(triphenylphosphine) palladium(0) (Pd(PPh3)4), [1,1'-Bis(diphenylphosphino) ferrocene] palladium (II) chloride (Pd(dppf)$_2$Cl$_2$), [1,2'-Bis (diphenylphosphino) ethane] palladium (II) chloride (Pd (dppe)2Cl$_2$), [1,3'-Bis(diphenylphosphino)propane] palladium (II) chloride (Pd(dppp)$_2$Cl$_2$), [1,4'-Bis (diphenylphosphino) butane] palladium (II) chloride (Pd (dppp)$_2$Cl$_2$).

As used herein, "alkylborate" means any compound containing C$_1$–C$_{10}$ alkyl groups bonded through an oxygen to boron to give a formula (alkyl—O—)$_3$B (a boronate ester) where the alkyl group is branched or a straight chain. Examples include, but are not limited to trimethyl, triethyl, tripropyl, triisopropyl, tributyl, triisobutyl, tri-sec-butyl, and tri-t-butylborate.

The compounds described herein may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. Methods on how to prepare optically active forms from optically active starting materials are known in the art, such as by resolution of racemic forms or by synthesis. All chiral, diastereomeric, racemic forms and all geometric isomeric forms of a structure are intended.

The present invention includes all isotopes of atoms occurring in the intermediates or final compounds. Isotopes include those atoms having the same atomic number but different mass numbers. By way of general example and without limitation isotopes of hydrogen include tritium and deuterium.

When any variable (for example but not limited to $R^1$, —$OR^{1e}$, etc.) occurs more than one time in any constituent or in any formula, its definition on each occurrence is independent of its definition at every other occurrence. Thus, for example, if a group is shown to be substituted with 0–3 $R^1$, then said group may optionally be substituted with up to three $R^1$, and $R^1$ at each occurrence is selected independently from the defined list of possible $R^1$.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substituent or substituents appears in a structure to be connected to the inside of a phenyl ring, those substituents may take any position which is chemically feasible, as a point of attachment on the phenyl ring.

As used herein, "alkyl" is intended to include both branched and straight-chain saturated aliphatic hydrocarbon groups having the specified number of carbon atoms; for example, $C_1$–$C_4$ alkyl includes methyl, ethyl, n-propyl, i-propyl, n-butyl, i-butyl, s-butyl, and t-butyl; for example $C_1$–$C_{10}$ alkyl includes $C_1$–$C_4$ alkyl, pentyl, hexyl, heptyl, octyl, nonyl, decyl, and isomer thereof.

As used herein, any carbon range such as "Cx–Cy" is intended to mean a minimum of "x" carbons and a maximum of "y" carbons representing the total number of carbons in the substituent to which it refers. For example, $C_4$–$C_{10}$ cycloalkylalkyll, could contain one carbon for "alkyl", and three for the cycloalkyl group, giving a total of four carbons; or a larger number of carbons for each alkyl group, or larger ring, not to exceed a total of ten carbons.

"Alkenyl" is intended to include hydrocarbon chains of either a straight or branched configuration and one or more unsaturated carbon-carbon bonds which may occur in any stable point along the chain, such as ethenyl, 1-propenyl, 2-propenyl, 1-butenyl, 2-butenyl, 3-butenyl, 1,3-butadienyl and the like. "Alkynyl" is intended to include hydrocarbon chains of either a straight or branched configuration and one or more triple carbon-carbon bonds which may occur in any stable point along the chain, such as ethynyl, propynyl, butynyl and the like.

As used herein, "cycloalkyl" is intended to include saturated ring groups, including mono-, bi-, or poly-cyclic ring systems, such as cyclopropyl, cyclobutyl, cyclopentyl, cyclohexyl, cycloheptyl, cyclooctyl, and adamantyl. As used herein, "cycloalkylalkyl" represents a cycloalkyl group attached through an alkyl bridge.

As used herein, "halo" or "halogen" refers to fluoro, chloro, bromo and iodo. "Haloalkyl" as used herein refers to an alkyl group containing a specified number of carbon atoms optionally substituted with halogens.

As used herein, "pharmaceutically acceptable salts" refer to derivatives of the disclosed compounds wherein the intermediates or final compound are modified by making acid or base salts of the intermediates or final compounds. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the intermediates or final compounds include the conventional non-toxic salts or the quaternary ammonium salts from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts are generally prepared by reacting the free base or acid with stoichiometric amounts or with an excess of the desired salt-forming inorganic or organic acid or base in a suitable solvent or various combinations of solvents.

The pharmaceutically acceptable salts of the acids of the intermediates or final compounds are prepared by combination with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The methods of the present invention, by way of example and without limitation, may be further understood by reference to Scheme 8. Scheme 8 provides the general synthetic scheme for the synthesis of compounds of formula (I).

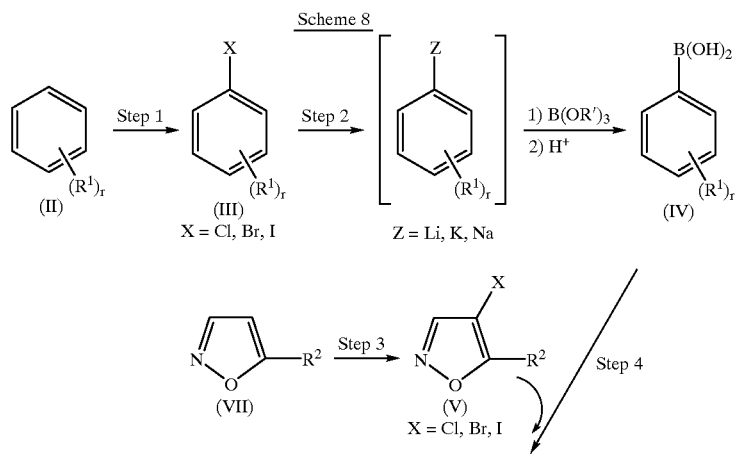

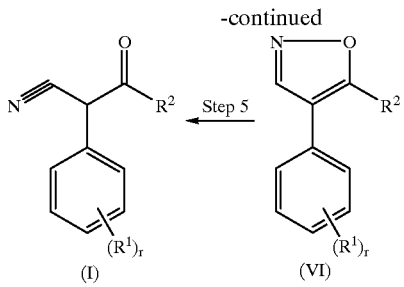

SYNTHESIS

In Step 1, a phenyl derivative undergoes a regioselective bromination. The halogenating agent is preferably dissolved in a suitable solvent. The amount of halogenating agent is preferably about 1.0 to about 1.2 equivalents. Preferred solvents include polar aprotic solvents, such as N,N-dimethylformamide, dimethylsulfoxide, and dimethylacetamide. N,N-Dimethylformamide is most preferred. The amount of solvent is preferably about 3 mLs to about 7 mLs per gram of starting material. The phenyl derivative is preferably added to this solution dropwise at a temperature of about −25° C. to about 40° C. Most preferred is about 20° C. to about 30° C. The reaction temperature is preferably maintained under about 20° C. to about 70° C. during the addition of the substrate. The resulting reaction mixture is preferably stirred at the preferred temperature for about 30 minutes to about 2 hours. More preferred is about 45 minutes to about 90 minutes. The reaction is considered complete preferably when the starting material is consumed, as evident by HPLC. A chromatograph of all reactions in the present invention may be obtained by performing an analysis on an aliquot of the reaction, preferably dissolved in one of the eluents. The reaction is preferably quenched by the addition of water and a suitable water immiscible organic solvent. Preferred solvents include hydrocarbons and ethers. Most preferred is heptane. The aqueous layer is preferably extracted with the organic solvent of choice and the organic layers are preferably combined. The organic layer is preferably washed with water to remove any residual polar aprotic solvent. The organic layer is preferably washed with an aqueous salt solution such as aqueous sodium chloride. The organic solution is preferably dried and concentrated. Numerous methods of drying are suitable, including the addition of drying agents such as sodium or magnesium sulfate and azeotropic distillation. The addition of a drying agent is preferred followed by filtration. The solvent may be removed under vacuum and the product may be purified by recrystallization or distillation, the choice of which will be readily understood by one skilled in the art.

In Step 2, the product of Step 1 undergoes a halogen exchange. The salt of the anion generated is reacted with an alkylborate species to give a boronate ester, which yields the boronic acid derivative when hydrolyzed. The product from Step 1, is preferably dissolved in a suitable aprotic solvent. While numerous solvents are possible, ethers and hydrocarbons are preferred. Tetrahydrofuran is most preferred. The preferred amount of solvent is about 3 mLs to about 10 mLs per gram of starting material. The solution is preferably cooled and treated dropwise with a solution of a strong base in a suitable solvent. Preferred bases include alkyl lithium bases. Butyllithium is most preferred. The preferred amount of base is about 1.0 equivalents to about 1.2 equivalents. The concentration of the base in the solvent is about 1.0 molar to about 2.6 molar. More preferred is about 2.4 molar to about 2.6 molar Preferable addition temperatures include about −78° C. to about −50° C. More preferred is about −70° C. to about −60° C. The resulting reaction mixture is preferably stirred at the preferred reduced temperature for a time sufficient to generate the phenyl anion, which is about 10 minutes to about 60 minutes. More preferred is about 15 minutes to about 40 minutes. The reaction is preferably treated dropwise with an alkylborate species. Most preferred is tri-isopropylborate. The preferred amount of alkylborate is about 1.0 equivalents to about 1.5 equivalents. Most preferred is about 1.1 equivalents to about 1.3 equivalents. The reaction mixture is preferably stirred at the reduced temperature for an additional period of time. Preferred is about 30 minutes to about 90 minutes. The reaction is preferably quenched at the reduced temperature with an aqueous acid. The preferred acid is saturated aqueous ammonium chloride solution. The resulting mixture is preferably gradually warmed to about −10° C. to about 10° C. for about 30 minutes to about 90 minutes and then preferably warmed to about 25° C. The layers are preferably separated, and the aqueous layer preferably extracted with a suitable, water immiscible organic solvent. The preferred solvent is ethyl acetate. More preferred is a mixture of ethyl acetate and tetrahydrofuran. The organic layers are preferably combined and washed with an aqueous salt solution such as aqueous sodium chloride. The organic solution is preferably dried and concentrated. Numerous methods of drying are suitable, including the addition of drying agents such as sodium or magnesium sulfate and azeotropic distillation. The addition of a drying agent is preferred followed by filtration. The solvent may be removed under vacuum and the product may be purified by recrystallization or distillation, the choice of which will be readily understood by one skilled in the art.

In Step 3, an isoxazole is selectively halogenated. While several halogenating agents may be used, iodine in the presence of a silver catalyst, N-iodosuccinimide (NIS), and N-bromosuccinimide (NBS) are preferred. When N-bromosuccinimide is used, the agent is preferably dissolved in a suitable solvent, of which polar aprotic are preferred. N,N-dimethylformamide and dimethyl sulfoxide are more preferred. N,N-dimethylformamide is most preferred. If N-iodosuccinimide is used, the agent is preferably dissolved in a suitable organic acid solvent, of which trifluoro acetic and trifluorosulfonic acid are preferred. Most preferred is trifluoroacetic acid. If iodine is used, halogenated solvents, of which chloroform is preferred. The amount of solvent used is preferably about 3 to about 10 mls of solvent per gram of halogenating agent. The solution is preferably treated with the substrate isoxazole at room temperature or at an elevated temperature up to the boiling point of the solvent employed. More preferred is performing the addition at a reaction temperature from about 25° C. to about 30° C.

Reaction temperature will affect the reaction rate, which will be readily understood by one skilled in the art. The reaction is considered complete preferably when the starting material is consumed, as evident by HPLC. By way of example, however, the bromination of 5-methylisoxazole using NBS reaches completion in about 20 hours to about 25 hours at the preferred temperature. The iodination using NIS in triflouroacetic acid reaches completion in about 2 hours to about 3 hours at the preferred temperature. The iodination using iodine and trifluorosilver acetate reaches completion in about 4 to about 5 hours at the preferred temperature. The halogenation occurs regioselectively at the C-4 position of isoxazole derivatives. Furthermore, 5-methylisoxazole gave no side chain brominated products under the present conditions. The crude halogenated product is preferably recovered by aqueous work-up. The reaction is preferably quenched with a suitable amount of water and a suitable water immiscible organic solvent. Numerous organic solvent are possible, of which chlorinated, ether, and hydrocarbon solvents are preferred. Heptane is most preferred. The reaction may generate succinimide which is preferably dissolved in the aqueous layer. If a polar aprotic solvent, or an organic acid is used in the reaction, it is preferably removed from the organic layer with repeated aqueous washing. The aqueous layer is preferably extracted with the organic solvent of choice and the organic layers are preferably combined. The organic layer may be washed with an aqueous salt solution such as aqueous sodium chloride. The organic solution is preferably dried and concentrated. Numerous methods of drying are suitable, including the addition of drying agents such as sodium or magnesium sulfate and azeotropic distillation. The addition of magnesium sulfate is preferred followed by fitration. The solvent may be removed under vacuum and the product may be purified, preferably by recrystallization in a suitable solvent, the choice of which will be readily understood by one skilled in the art.

In Step 4, the product from Step 2 and Step 3 are coupled in the presence of a catalyst to give a phenyl-isoxazole system. A mixture of the isoxazole derivative produced in Step 3, and the boronic acid derivative produced in Step 2 are preferably mixed with a suitable aqueous base in a suitable solvent. Preferably, the amount of the boronic acid derivative is about 1.0 equivalents to about 1.2 equivalents. While numerous solvents may be used, hydrocarbons and ethers are preferred with water mixtures of these solvents being preferred. More preferred is water mixtures with toluene, dimethoxyethane (DME), acetonitrile, and tetrahydrofuran. Dimethoxyethane and water is most preferred. Preferably, mixtures of solvents contain about equal amounts of each component, with the total amount preferably about 5 to about 20 mL per gram of each starting material. A phosphate buffer with a pH of about 7 to about 10 or sodium bicarbonate is preferred as the base. The amount of base may vary in range with about 1.0 equivalents to about 5.0 equivalents being preferred. About 2.0 to about 4.0 is more preferred. Even more preferred is sodium bicarbonate buffered to a pH of about 8 to about 9 with a phosphate buffer. Additional water may be added. The vessel may be degassed by purging with an inert gas. The solution is then preferably treated with a suitable catalyst at about 20° C. to about 30° C. Preferred catalysts include those known in the art to facilitate a Suzuki coupling, such as palladium (O) catalysts. More preferred is Pd(dppf)$_2$Cl$_2$ or Pd(PPh3)4. Most preferred is Pd(dppf)$_2$Cl$_2$. The reaction rate will be affected by the amount of catalyst used, which will be readily understood by one skilled in the art. The amount of catalyst may be from about 0.1% to about 10% by weight. More preferred is about 0.1% to about 3% by weight. Most preferred is about 0.5% to about 1.0% by weight. The resulting reaction mixture may be degassed. The solution is preferably warmed to about 60° C. to about 100° C. More preferred is about 75° C. to about 90° C. The reaction is considered complete preferably when the starting material is consumed, as evident by HPLC. The reaction temperature is then preferably cooled down to room temperature, before preferably being treated with an equal volume of water and a suitable water immiscible organic solvent. While many solvents may be used, ethers such as diethyl ether, t-butyl methyl ether or hydrocarbons such as heptane, hexane, pentane and toluene are preferred. Most preferred is t-butyl methyl ether. The two layers are preferably separated, and the aqueous layer was extracted with a water immiscible organic solvent. The aqueous layer is preferably extracted with the organic solvent and the organic layers are preferably combined. The organic layer may be washed with an aqueous salt solution such as aqueous sodium chloride. The organic solution is preferably dried and concentrated. Numerous methods of drying are suitable, including the addition of drying agents such as sodium or magnesium sulfate and azeotropic distillation. The addition of magnesium sulfate is preferred followed by fitration. The solvent may be removed under vacuum and the product may be purified, preferably by recrystallization in a suitable solvent, the choice of which will be readily understood by one skilled in the art.

In Step 5, the isoxazole system is opened with an isomerization base to give an α-aryl-β-ketonitrile. The crude material may be used directly in the following base-promoted isomerization reaction. The product of Step 4 is preferably dissolved in a protic solvent. Preferred are methanol, ethanol and isopropanal. Most preferred is methanol. The solution is preferably treated dropwise with a solution of a base. Alkoxide bases are preferred with sodium methoxide being most preferred. The amount of base is preferably about 1.0 to about 1.5 equivalents. More preferred is about 1.2 to about 1.4 equivalents. The base is preferably dissolved in a complimentary solvent to give a weight percent concentration of about 10% to about 50%. More preferred is about 20% to about 30%. Most preferred is a solution of about 25% sodium methoxide in methanol. The solution is preferably stirred at about 20° C. to about 30° C. The resulting reaction mixture is preferably stirred at this temperature for about 1 hour to about 8 hours. More preferred is about 2 to about 5 hours. The reaction is considered complete preferably when the starting material is consumed, as evident by HPLC. The reaction is preferably quenched by the addition of an equal volume of water and a suitable organic solvent. While numerous solvents may be used, ethers are preferred. Most preferred is t-butylmethyl ether. The two layers are preferably separated, and the aqueous layer may be extracted with a water immiscible organic solvent. The aqueous layer may be cooled, and is preferably treated dropwise with an aqueous acid. While numerous acids may be used, hydrochloric acid with a concentration of about 1 normal to about 6 normal is preferred. The addition of acid is preferably accompanied by monitoring the pH of the solution. The addition is complete when the pH is preferably about 5 to about 6. The solution is preferably extracted with the organic solvent and the combined organic extracts combined. The organic layer may be washed with an aqueous salt solution such as aqueous sodium chloride. The organic solution is preferably dried and concentrated. Numerous methods of drying are suitable, including the addition of drying agents such as sodium or magnesium sulfate and azeotropic distillation. The addition of magnesium sulfate is preferred followed by fitration. The solvent may be removed under vacuum and the product may be purified, preferably by recrystallization in a suitable solvent, the choice of which will be readily understood by one skilled in the art.

The present invention may be further exemplified without limitation by reference to Scheme 9.

mixture was stirred at room temperature for an additional 30 min before being treated with $H_2O$ (1000 mL) and heptane (1000 mL). The two layers were separated, and the aqueous layer was extracted with heptane (200 mL). the combined organic extracts were washed with $H_2O$ (3×500 mL), saturated $NaHCO_3$ (500 mL), and saturated NaCl (500 mL), dried over $MgSO_4$, and concentrated in vacuo. The crude

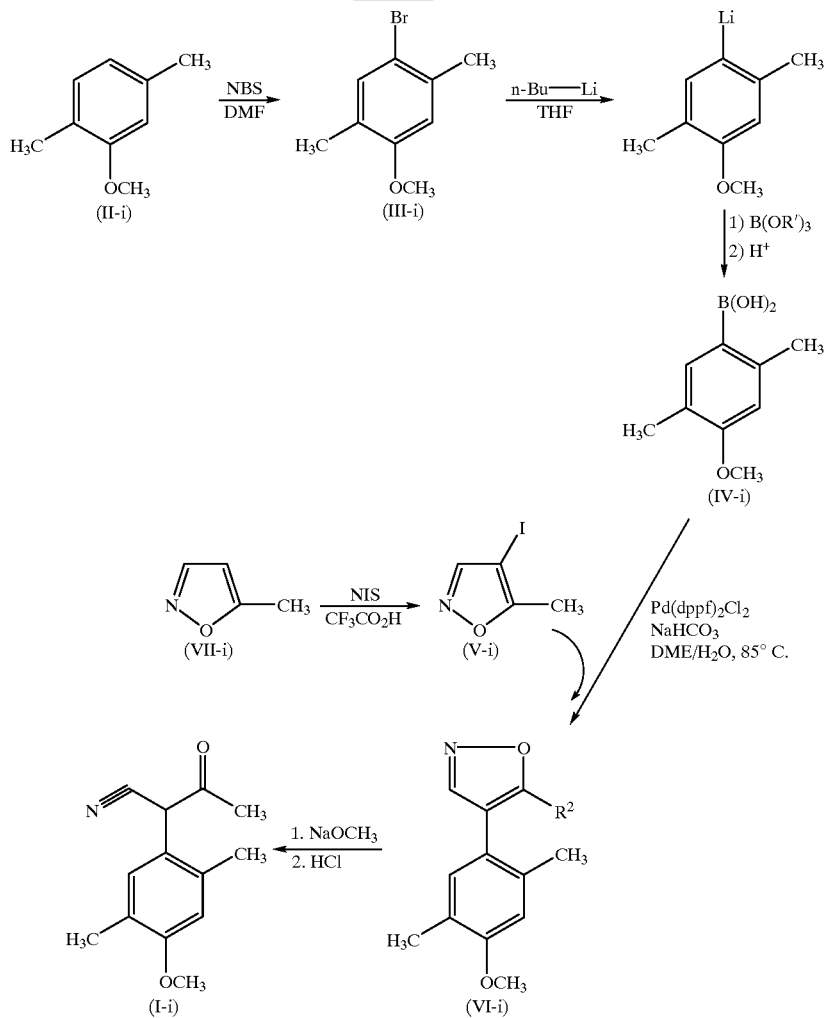

product (2, 164.2 g, 176.8 g theoretical, 92.9%) was obtained as yellow to brown oil, which solidified at room temperature.

EXAMPLE 1

4-Iodo-5-methylisoxazole (2)

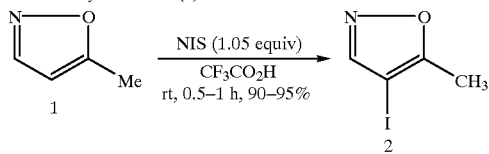

A solution of NIS (200 g, 0.888 mol, 1.0 equiv) in $CF_3CO_2H$ (340 mL) was treated dropwise with 5-methylisoxazole (1, 70.26 g, 0.846 mol) at 25° C. under $N_2$. The reaction temperature was maintained under 55° C. during the addition of 5-methylisoxazole. The resulting reaction

EXAMPLE 2

4-Iodo-5-methylisoxazole (2)

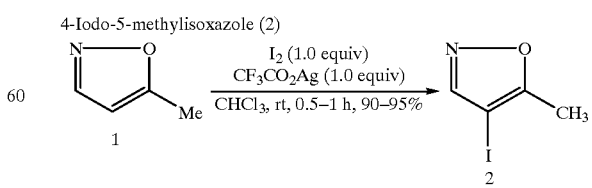

A solution of $CF_3CO_2Ag$ (11.0 g, 50 mmol, 1.0 equiv) in $CHCl_3$ (100 mL) was treated with 5-methylisoxazole (1, 45.15 g, 50 mmol), and the resulting reaction mixture was treated with a solution of I$_2$ (12.7 g, 50 mmol, 1.0 equiv) in CHCl$_3$ (100 mL) at 25° C. under N$_2$. The reaction mixture was then warmed to 40–45° C. for 4 h. Filtration of the cooled reaction mixture and the solids were washed with CH$_2$Cl$_2$ (2×50 mL). The filtrates were then washed with water (2×50 mL) and saturated NaCl aqueous solution (50 mL), dried over MgSO$_4$, and concentrated in vacuo. The crude product (2, 10.04 g, 10.45 g theoretical, 96%) was obtained as a thick oil.

EXAMPLE 3

4-Bromo-5-methylisoxazole (3).

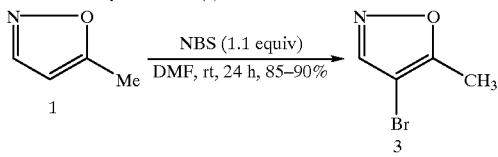

A solution of NBS (97.9 g, 0.55 mol, 1.1 equiv) in DMF (500 mL) was treated dropwise with 5-methylisoxazole (1, 41.5 g, 0.5 mol) at 25° C. under N$_2$. The resulting reaction mixture was stirred for an additional 24 h at room temperature before being treated with H$_2$O (1000 mL) and heptane (1000 mL). The aqueous layer was extracted with heptane (500 mL), and the combined organic extracts were washed with H$_2$O (4×400 mL), and saturated NaCl solution (400 mL), dried over MgSO$_4$, and concentrated in vacuo. The crude product (3, 71.4 g, 81.0 g theoretical, 88.1%) was obtained as a pale-yellow oil.

EXAMPLE 4

4-Bromo-2,5-dimethylanisole (5)

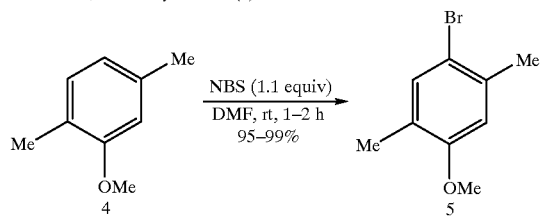

A solution of NBS (306.9 g, 1.724 mol, 1.1 equiv) in DMF (850 mL) was treated dropwise with 2,5-dimethylanisole (4, 213.2 g, 220.9 mL, 1.567 mol) at 25° C. under N$_2$. The reaction temperature was maintained under 60° C. during the addition of 2,5-dimethylanisole. The resulting reaction mixture was stirred at room temperature for an additional 1 h before being treated with H$_2$O (2000 mL) and heptane (1000 mL). The two layers were separated and the aqueous layer was extracted with heptane (500 mL). The combined organic extracts were washed with H$_2$O (4×800 mL), and saturated NaCl solution (500 mL), dried over MgSO$_4$, and concentrated in vacuo. The crude product (5, 329.8 g, 336.9 g theoretical, 97.9%) was obtained as pale-yellow oil.

EXAMPLE 5

2,5-Dimethyl-4-methoxybenzeneboronic acid (6)

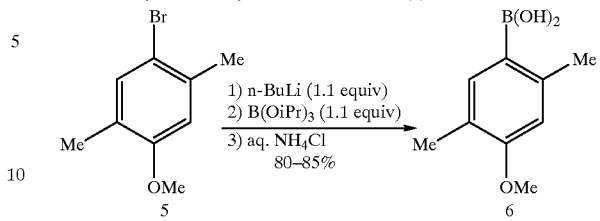

A solution of 4-bromo-2,5-dimethylanisole (5, 172 g, 0.8 mol) in anhydrous THF (800 ml) was treated dropwise with a solution of n-butyl lithium (2.5 M solution in hexane, 352 mL, 0.88 mol. 1.1 equiv) in hexane at −60–65° C. under N$_2$. The resulting reaction mixture was stired at −60–65° C. for an additional 30 min before being treated dropwise with B(OiPr)$_3$ (165.44 g, 203.2 mL, 0.88 mol, 1.1 equiv) at −60 to −65° C. The reaction mixture was stirred at −60 to −65° C. for an additional 1 h. The reaction was then quenched with saturated NH$_4$Cl aqueous solution (750 mL) at −60 to −65° C., and the resulting mixture was gradually warmed to 0° C. for 1 h and subsequently to room temperature. The two layers were separated, and the aqueous layer was extracted with EtOAc/THF (1:1, 400 mL). The combined organic extracts were then washed with H$_2$O (400 mL), and saturated NaCl solution (400 mL), dried over MgSO$_4$, and concentrated in vacuo. The residual white solids were then suspended in heptane (500 mL), and the resulting suspension was stirred at room temperature for 30 min. The solids were collected by filtration and washed with heptane (2×200 mL), dried in vacuo at 40–45° C. for overnight. The crude product (6, 116.7 g, 144.0 g theoretical, 81%) was obtained as a white powder.

EXAMPLE 6

4-Methoxy-2-methylbenzeneboronic acid (8)

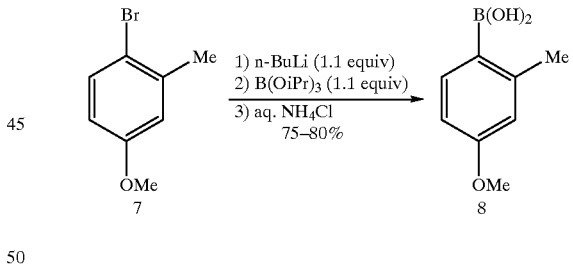

A solution of 4-bromo-3-methylanisole (7, 92 g, 0.457 mol) in anhydrous THF (400 ml) was treated dropwise with a solution of n-butyl lithium (2.5 M solution in hexane, 201 mL, 0.503 mol, 1.1 equiv) in hexane at −60—65° C. under N$_2$. The resulting reaction mixture was stired at −60—65° C. for an additional 30 min before being treated dropwise with B(OiPr)$_3$ (94.56 g, 116 mL, 0.503 mol, 1.1 equiv) at −60—65° C. The reaction mixture was stirred at −60—65° C. for an additional 1 h. The reaction was then quenched with saturated NH$_4$Cl aqueous solution (400 mL) at −60—65° C., and the resulting mixture was gradually warmed to 0° C. for 1 h and subsequently to room temperature. The two layers were separated, and the aqueous layer was extracted with EtOAc/THF (1:1, 200 mL). The combined organic extracts were then washed with H$_2$O (200 mL), and saturated NaCl aqueous solution (200 mL), dried over MgSO$_4$, and concentrated in vacuo. The residual white solids were then suspended in heptane (400 mL), and the resulting suspension was stirred at room temperature for 30 min. The solids were collected by filtration and washed with heptane (2×100 mL), dried in vacuo at 40–45° C. for overnight. The crude product (8, 57.9 g, 75.86 g theoretical, 76.3%) was obtained as a white powder.

EXAMPLE 7

(2,5-Dimethyl-4-methoxy)phenyl-5-methylisoxazole (9)

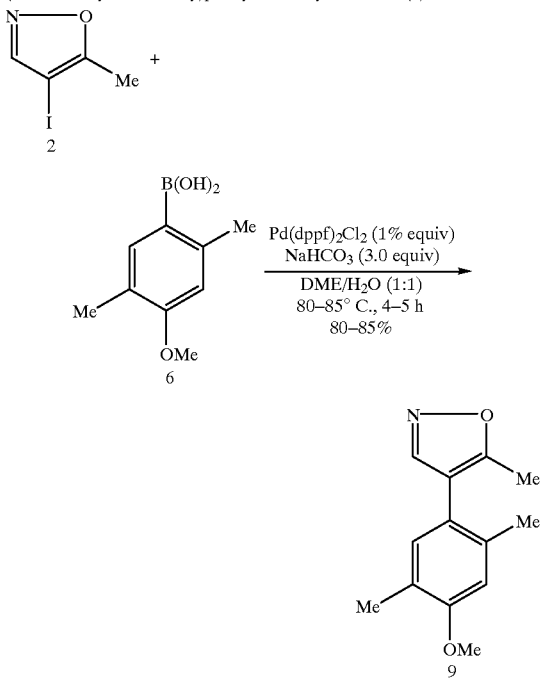

A mixture of 4-iodo–5-methylisoxazole (2, 4.18 g, 20 mmol), 2,5-dimethyl–4-methoxybenzeneboronic acid (6, 3.96 g, 22 mmol, 1.1 equiv), and NaHCO$_3$ (5.04 g, 60 mmol, 3.0 equiv) in DME (15 mL) and H$_2$O (15 mL) was treated with Pd(dppf)$_2$Cl$_2$ (163.2 mg, 0.2 mmol, 1% equiv) at 25° C. under N$_2$, and the resulting reaction mixture was degassed for three times. The resulting reaction mixture was warmed to 80–85° C. for 4 h, which was then cooled down to room temperature before being treated with TBME (40 mL) and H$_2$O (40 mL). The two layers were separated, and the aqueous layer was extracted with TBME (2×30 mL). The combined organic extracts were then washed with H$_2$O (2×20 ml), and saturated aqueous NaCl (20 mL), dried over MgSO$_4$, and concentrated in vacuo. The residue was then purified by flash chromatography (SiO$_2$, 5–15% EtOAc-hexane gradient elution) to afford the desired Suzuki coupling product (9, 3.52 g, 4.34 g theoretical, 81.1%) as a colorless oil.

EXAMPLE 8

(4-Methoxy-2-methyl)phenyl-5-methylisoxazole (11)

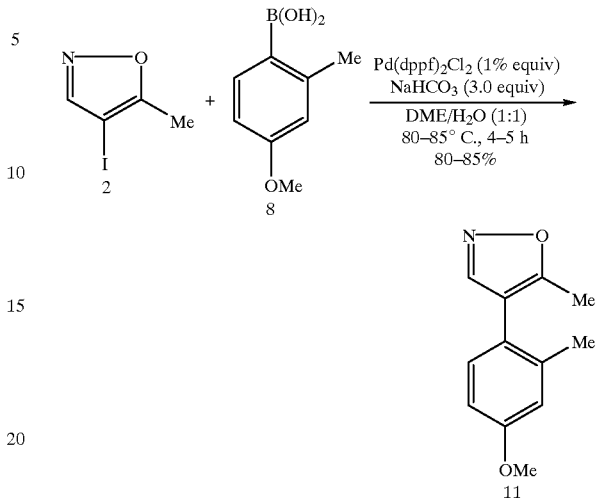

A mixture of 4-iodo-5-methylisoxazole (2, 2.09 g, 10 mmol), 4-methoxy-2-methylbenzeneboronic acid (8, 1.826 g, 11 mmol, 1.1 equiv), and NaHCO3 (2.52 g, 30 mmol, 3.0 equiv) in DME (8 mL) and H$_2$O (8 mL) was treated with Pd(dppf)$_2$Cl$_2$ (82 mg, 0.1 mmol, 1% equiv) at 25° C. under N$_2$, and the resulting reaction mixture was degassed for three times. The resulting reaction mixture was warmed to 80–85° C. for 4 h, which was then cooled down to room temperature before being treated with TBME (40 mL) and H$_2$O (40 mL). The two layers were separated, and the aqueous layer was extracted with TBME (2×20 mL). The combined organic extracts were then washed with H$_2$O (2×20 ml), and saturated aqueous NaCl (20 mL), dried over MgSO$_4$, and concentrated in vacuo. The residue was then purified by flash chromatography (SiO$_2$, 5–15% EtOAc-hexane gradient elution) to afford the desired Suzuki coupling product (11, 1.71 g, 2.03 g theoretical, 84.2%) as a colorless oil.

EXAMPLE 9

α-Acetyl-α-(2,5-dimethyl-4-methoxy)phenylacetonitrile (13)

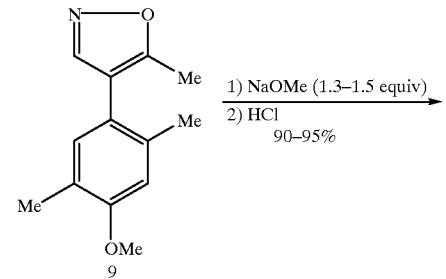

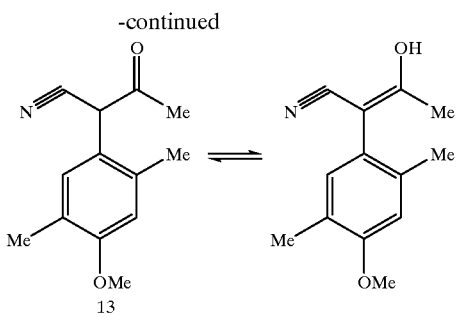

A solution of pure 4-(2,5-dimethyl-4-methoxy)phenyl-5-methylisoxazole (9, 1.085 g, 5 mmol) in MeOH (10 mL) was treated dropwise with a solution of MeONa (25% w/w solution in methanol, 1.62 g, 1.7 mL, 7.5 mmol, 1.5 equiv) at room temperature under N$_2$. The resulting reaction mixture was stirred at room temperature for 4 h before being treated with H$_2$O (20 mL) and TBME (20 mL). The resulting mixture was then stirred at room temperature for 10 min. The two layers were separated, and the aqueous layer was extracted with TBME (10 mL). The aqueous layer was then cooled down to 10–15° C. and treated dropwise with 4 N HCl aqueous solution to pH 5–6 at 10–15° C. before being extracted with TBME (2×30 mL). The combined organic extracts were then washed with H$_2$O (20 mL), saturated NaHCO$_3$ aqueous solution (10 mL), and saturated NaCl aqueous solution (10 mL), dried over MgSO$_4$, and concentrated in vacuo. The crude desired product (13, 1.0 g, 1.085 g theoretical, 92%) was obtained as a yellow to brown oil, which was found to be a mixture of keto and enol form (about 4 to 7 in CDCl$_3$) in solution.

EXAMPLE 10

α-Acetyl-α-(2,5-dimethyl-4-methoxy)phenylacetonitrile (13).

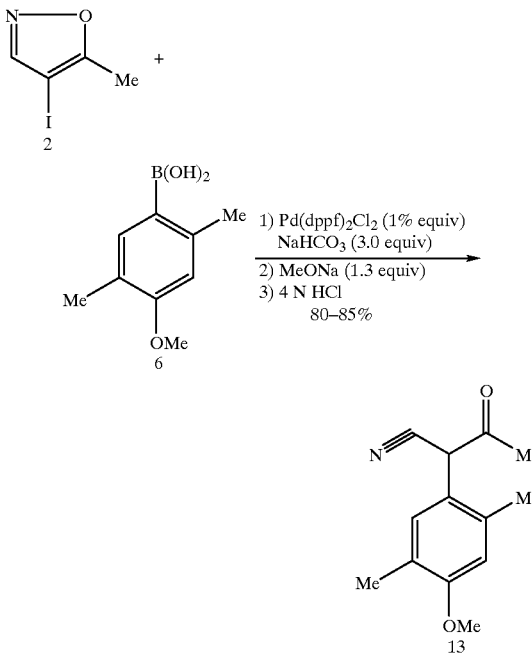

A mixture of 4-iodo-5-methylisoxazole (2, 52.25 g, 0.25 mol), 2,5-dimethyl-4-methoxybenzeneboronic acid (6, 49.5 g, 0.275 mmol, 1.1 equiv), and NaHCO$_3$ (63 g, 0.75 mol, 3.0 equiv) in DME (175 mL) and H$_2$O (175 mL) was treated with Pd(dppf)$_2$Cl$_2$ (2.04 g, 2.5 mmol, 1% equiv) at 25° C. under N$_2$, and the resulting reaction mixture was degassed for three times before being warmed to 80–85° C. for 4 h. The reaction mixture was cooled down to room temperature before being treated with TBME (300 mL) and H$_2$O (300 mL). The two layers were separated, and the aqueous layer was extracted with TBME (200 mL). The combined organic extracts were then washed with H$_2$O (2×150 mL), and saturated aqueous NaCl (150 mL), dried over MgSO$_4$, and concentrated in vacuo. The crude brown oil was directly used in the following base-promoted isomerization reaction. The crude brown oil obtained from Suzuki coupling reaction was dissolved in MeOH (300 mL) and treated dropwise with a solution of MeONa (25% w/w solution in methanol, 70.2 g, 74 mL, 0.325 mol, 1.3 equiv) at room temperature under N$_2$. The resulting reaction mixture was stirred at room temperature for 4 h before being treated with H$_2$O (300 mL) and TBME (300 mL). The resulting mixture was then stirred at room temperature for 10 min. The two layers were separated, and the aqueous layer was extracted with TBME (100 mL). The aqueous layer was then cooled down to 10–15° C. and treated dropwise with 4 N HCl aqueous solution (88 mL, 0.35 mol, 1.4 equiv) to pH 5–6 at 10–15° C. before being extracted with TBME (2×300 mL). The combined organic extracts were then washed with H$_2$O (2×150 mL), saturated NaHCO$_3$ aqueous solution (100 mL), and saturated NaCl aqueous solution (100 mL), dried over MgSO$_4$, and concentrated in vacuo. The crude desired product (13, 44.6 g, 54.25 g theoretical, 82.2% for two steps) was obtained as a yellow to brown oil.

EXAMPLE 11

α-Acetyl-α-(4-methoxy-2-methyl)phenylacetonitrile (14)

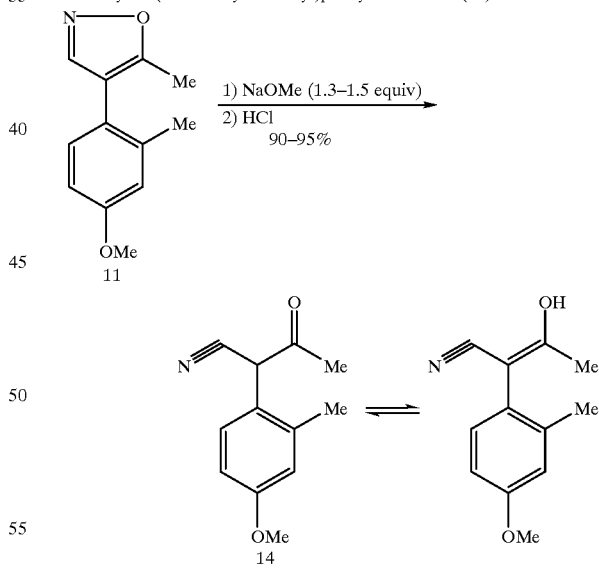

A solution of pure 4-(4-methoxy-2-methyl)phenyl-5-methylisoxazole (11, 2.03 g, 10 mmol) in MeOH (20 mL) was treated dropwise with a solution of MeONa (25% w/w solution in methanol, 3.24 g, 3.4 mL, 15 mmol, 1.5 equiv) at room temperature under N$_2$. The resulting reaction mixture was stirred at room temperature for 4 h before being treated with H$_2$O (40 mL) and TBME (40 mL). The resulting mixture was then stirred at room temperature for 10 min. The two layers were separated, and the aqueous layer was extracted with TBME (20 mL). The aqueous layer was then cooled down to 10–15° C. and treated dropwise with 4 N HCl aqueous solution to pH 5–6 at 10–15° C. before being extracted with TBME (2×50 mL). The combined organic extracts were then washed with H$_2$O (30 mL), saturated NaHCO3 aqueous solution (20 mL), and saturated NaCl aqueous solution (20 mL), dried over MgSO$_4$, and concentrated in vacuo. The crude desired product (14, 1.91 g, 2.03 g theoretical, 94.1%) was obtained as a yellow to brown oil, which was found to be a mixture of keto and enol form (about 5 to 1 in CDCl$_3$) in solution.

EXAMPLE 12

α-Acetyl-α-(4-methoxy-2-methyl)phenylacetonitrile(14)

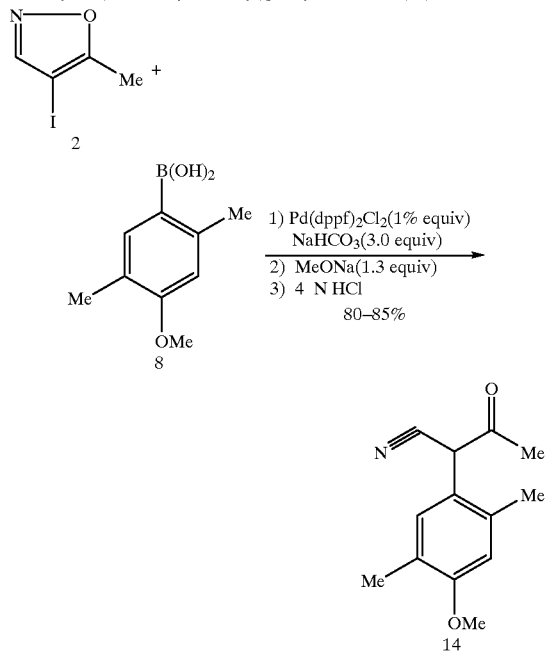

A mixture of 4-iodo-5-methylisoxazole (2, 41.8 g, 0.2 mol), 4-methoxy-2-methylbenzeneboronic acid (8, 36.52 g, 0.22 mmol, 1.1 equiv), and NaHCO$_3$ (50.4 g, 0.6 mol, 3.0 equiv) in DME (140 mL) and H$_2$O (140 mL) was treated with Pd(dppf)$_2$Cl$_2$ (1.633 g, 2.0 mmol, 1% equiv) at 25° C. under N$_2$, and the resulting reaction mixture was degassed for three times before being warmed to 80–85° C. for 4 h. The reaction mixture was cooled down to room temperature before being treated with TBME (250 mL) and H$_2$O (250 mL). The two layers were separated, and the aqueous layer was extracted with TBME (200 mL). The combined organic extracts were then washed with H$_2$O (2×100 mL), and saturated aqueous NaCl (100 mL), dried over MgSO$_4$, and concentrated in vacuo. The crude brown oil was directly used in the following base-promoted isomerization reaction. The crude brown oil obtained from Suzuki coupling reaction was dissolved in MeOH (250 mL) and treated dropwise with a solution of MeONa (25% w/w solution in methanol, 56.16 g, 59 mL, 0.26 mol, 1.3 equiv) at room temperature under N$_2$. The resulting reaction mixture was stirred at room temperature for 4 h before being treated with H$_2$O (250 mL) and TBME (250 mL). The resulting mixture was then stirred at room temperature for 10 min. The two layers were separated, and the aqueous layer was extracted with TBME (100 mL). The aqueous layer was then cooled down to 10–15° C. and treated dropwise with 4 N HCl aqueous solution (70 mL, 0.28 mol, 1.4 equiv) to pH 5–6 at 10–15° C. before being extracted with TBME (2×250 mL). The combined organic extracts were then washed with H$_2$O (150 mL), saturated NaHCO$_3$ aqueous solution (100 mL), and saturated NaCl aqueous solution (100 mL), dried over MgSO$_4$, and concentrated in vacuo. The crude desired product (14, 33.3 g, 40.6 g theoretical, 82% for two steps) was obtained as a yellow to brown oil, which was found to be pure enough to do the next reaction.

| HPLC CONDITIONS (MF002DE): | |
|---|---|
| Column: | 25 cm × 4.6 mm id. Ultracarb 5 C8 (Phenomenex) |
| Mobile Phase: | A: 0.1% trifluoroacetic acid in HPLC grade water |
| | B: 0.1% trifluoroacetic acid in HPLC grade acetonitrile |
| Gradient: | t = 0 min    60% A 40% B |
| | t = 5 min    60% A 40% B |
| | t = 10 min   60% A 40% B |
| | t = 15 min   55% A 45% B |
| | t = 20 min   50% A 50% B |
| | t = 25 min    0% A 100% B |
| | t = 30 min    0% A 100% B |
| Flow Rate: | 1.0 mL/min |
| Injection Volume: | 5 microliters |
| Stop Time: | 30 minutes |
| Post Time: | 5 minutes |
| Oven Temp.: | ambient |
| Detector: | UV (220 nm) |

Sample Prep.: Dissolve 25 mg of sample (dry solids weight) in to a sutable solvent adjust concentration to approximately 1 mg/ml. The sample concentration may be adjusted to ensure the proper quantitation.

What is claimed is:

1. A process for the preparation of a compound of formula (I):

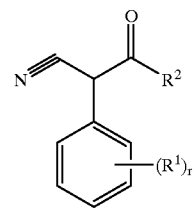

or a pharmaceutically acceptable salt form thereof;
wherein:
  r is an integer from 0 to 4;
  $R^1$ is independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NR^{1c}R^{1d}$, —$OR^{1e}$ and —$SR^{1e}$;
  $R^{1c}$ and $R^{1d}$ are independently selected at each occurrence from the group consisting of:
    H, $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl;
  alternatively, $R^{1c}$ and $R^{1d}$ are taken together to form a heterocyclic ring selected from the group consisting of:
    piperidine, pyrrolidine, piperazine, N-methylpiperazine, morpholine and thiomorpholine, each heterocyclic ring optionally substituted with 1–3 $C_1$–$C_4$ alkyl groups;

$R^{1e}$ is independently selected at each occurrence from the group consisting of:
  H, $C_1$–$C_{10}$ alkyl, $C_3$–$C_6$ cycloalkyl, and $C_4$–$C_6$ cycloalkylalkyl;

$R^2$ is selected from the group consisting of:
  H, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, $C_1$–$C_4$ haloalkyl, and $C_1$–$C_4$ alkyl substituted with 0–5 $R^{2a}$;

$R^{2a}$ is independently selected at each occurrence from the group consisting of:
  H, $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, halo, CN, $C_1$–$C_4$ haloalkyl, —$OR^{2e}$, and —$SR^{2e}$; and $R^{2e}$ is independently selected at each occurrence from the group consisting of:
  H, $C_1$–$C_{10}$ alkyl, $C_3$–$C_6$ cycloalkyl, and $C_4$–$C_6$ cycloalkylalkyl;

the process comprising the steps of:
(1) contacting the compound of formula (II):

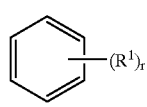

(II)

with a halogenating agent to form a compound of formula (III):

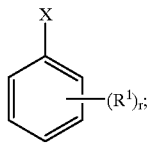

(III)

wherein X is a halogen derived form the halogenating agent;

(2) contacting the compound of formula (III) with a strong base followed by addition of an alkylborate to form a compound of formula (IV):

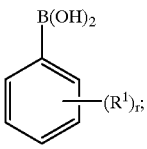

(IV)

(3) contacting the compound of formula (IV) with a compound of formula (V):

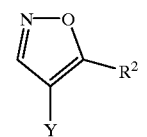

(V)

wherein Y second halogen;
in the presence of a catalyst and a weak base to form a compound of formula (VI):

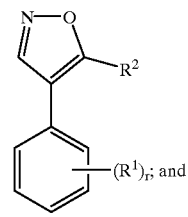

(VI)

(4) contacting the compound of formula (VI) with an isomerization base to form a compound of formula (I), or a pharmaceutically acceptable salt form thereof.

2. The process of claim 1, wherein:
r is an integer from 0–3;
X is bromine;
Y is iodine;
$R^1$ is independently selected at each occurrence from the group consisting of:
  H, methyl and methoxy; and
$R^2$ is methyl.

3. The process of claim 1, wherein:
in step 1, the halogenating agent is N-bromosuccinimide;
X is bromine;
in step 2, the alkylborate is selected from the group consisting of:
  trimethylborate, triethylborate, tripropylborate, triisopropylborate, tributylborate, triisobutylborate, tri-sec-butylborate, and tri-t-butylborate;

the strong base is selected from the group consisting of:
  isobutyllithium, n-hexyllithium, n-octyllithium, n-butyllithium, s-butyllithium, t-butyllithium, phenyllithium and triphenylmethyllithium;

in step 3, the weak base is a phosphate buffer having a pH of about 7 to about 10 or sodium bicarbonate;
Y is iodine;
the catalyst is tetrakis(triphenylphosphine) palladium(0) or [1,1'-Bis(diphenylphosphino)ferrocene] palladium (II) chloride; and in step 4, the isomerization base is selected from the group consisting of:
  lithium methoxide, sodium methoxide, potassium methoxide, lithium ethoxide, sodium ethoxide, potassium ethoxide, lithium tert-butoxide, sodium tert-butoxide, and potassium tert-butoxide.

4. The process of claim 2, wherein:
in step 1, the halogenating agent is N-bromosuccinimide;
in step 2, the alkylborate is triisopropylborate, and the strong base is n-butyllithium;
in step 3, the catalyst is [1,1'-Bis(diphenylphosphino)ferrocene] palladium (II) chloride, and the weak base is sodium bicarbonate; and
in step 4, the isomerization base is sodium methoxide.

* * * * *